United States Patent [19]

Cross et al.

[11] 4,259,345

[45] Mar. 31, 1981

[54] 2-(IMIDAZOL-1-YLMETHYL)PYRROLES

[75] Inventors: Peter E. Cross, Canterbury; Roger P. Dickinson, Dover, both of England

[73] Assignee: Pfizer Inc., New York, N.Y.

[21] Appl. No.: 123,242

[22] Filed: Feb. 21, 1980

[30] Foreign Application Priority Data

Feb. 24, 1979 [GB] United Kingdom ............... 06617/79

[51] Int. Cl.³ .................... A61K 31/415; C07D 403/06
[52] U.S. Cl. .................................. 424/273 R; 548/336
[58] Field of Search ..................... 548/336; 424/273 R

[56] References Cited

U.S. PATENT DOCUMENTS 4,115,578   9/1978   Miller et al. .................... 548/336

FOREIGN PATENT DOCUMENTS 3560   8/1979   European Pat. Off. .

*Primary Examiner*—Henry R. Jiles
*Assistant Examiner*—Natalia Harkaway
*Attorney, Agent, or Firm*—Francis X. Murphy; Charles J. Knuth; Peter C. Richardson

[57] ABSTRACT

Novel 2-(Imidazol-1-ylmethyl)pyrroles and pharmaceutically acceptable acid addition salts thereof are disclosed. The novel compounds are useful in selectively inhibiting the action of the thromboxane synthetase enzyme.

8 Claims, No Drawings

2-(IMIDAZOL-1-YLMETHYL)PYRROLES

BACKGROUND OF THE INVENTION

This invention relates to certain pyrrole derivatives, specifically, to certain 2-(imidazol-1-ylmethyl)pyrroles, and to their use in selectively inhibiting the action of the thromboxane synthetase enzyme, i.e. without significantly inhibiting the action of the prostacyclin synthetase or cyclo-oxygenase enzyme. The compounds may thus be useful in, for example, the treatment of ischaemic heart disease, stroke, transient ischaemic attack, migraine and the vascular complications of diabetes.

SUMMARY OF THE INVENTION

Thus according to the invention there is provided a compound of the formula:

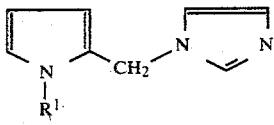 (I)

wherein $R^1$ is lower cycloalkyl, lower cycloalkyl-lower alkyl, lower alkenyl-lower alkyl, lower alkanoyl, phenyl, lower cycloalkylcarbonyl, or a group of the formula:

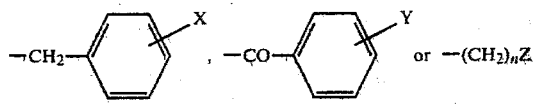

wherein
X is hydrogen, carboxy or lower alkoxycarbonyl;
Y is hydrogen, lower alkyl, lower alkoxy or halogen;
n is an integer of from 1 to 4; and
Z is cyano, carboxy or lower alkoxycarbonyl; and the pharmaceutically acceptable acid addition salts thereof.

In this specification, the term "lower" when applied to an alkyl, alkoxy, alkenyl, or alkanoyl group means that the group contains not more than 4 carbon atoms, where appropriate, in a straight or branched chain, and when applied to a cycloalkyl group, means that the group contains not more than 6 carbon atoms. The term "halogen" means fluorine, chlorine, bromine or iodine.

In addition the invention provides a pharmaceutical composition comprising a compound of the formula (I) or a pharmaceutically acceptable acid addition salt thereof, together with a pharmaceutically acceptable diluent or carrier. The composition is preferably in unit dosage form.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), a pharmaceutically acceptable acid addition salt thereof, or a pharmaceutical composition comprising such a compound or salt together with a pharmaceutically acceptable diluent or carrier.

The invention yet further provides a compound of the formula (I) or a pharmaceutically acceptable acid addition salt thereof for use in treating an animal, including a human being, to inhibit the action of the thromboxane synthetase enzyme without significantly inhibiting the action of the prostacyclin synthetase or cyclo-oxygenase enzymes.

In one aspect of the invention $R^1$ is lower cycloalkyl, lower cycloalkyl-lower alkyl, lower alkenyl-lower alkyl, lower alkanoyl, phenyl, benzyl or a group of the formula:

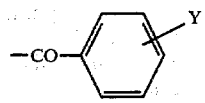

wherein Y is as defined above.

The preferred compounds are those in which $R^1$ is allyl; cyclopropylmethyl; benzoyl optionally mono-substituted by methyl, methoxy or chloro; acetyl; cyclopropylcarbonyl; phenyl; cyclohexyl; 2-cyanoethyl; 2-carboxyethyl; or benzyl optionally monosubstituted on the phenyl ring by carboxy or ethoxycarbonyl.

In the preferred individual compound $R^1$ is:

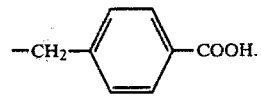

By the term "unit dosage form" as used herein is meant a physically discrete unit containing an individual quantity of the active component in association with a pharmaceutically acceptable diluent or carrier, the quantity of active component being such that at least one unit or severable fraction of a unit is required for a single therapeutic administration. In the case of severable units, such as scored tablets, at least one severable fraction such as a ½ or ¼ of the unit may be all that is required for a single therapeutic administration. It will be appreciated that the term "unit dosage form" does not include mere solutions except when the solutions are packaged in ingestible containers, e.g. soft capsules, or have been prepared so as to be suitable for parenteral administration, e.g. in vials of solution suitable for parenteral injection.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate, and p-toluene sulphonate salts.

DETAILED DESCRIPTION OF THE INVENTION

The compounds of the invention may be prepared by a number of routes, including the following:

(1) The compounds of the invention in which $R^1$ is other than lower alkanoyl, optionally substituted benzoyl, or lower cycloalkylcarbonyl may be prepared by reacting a pyrrole of the formula:

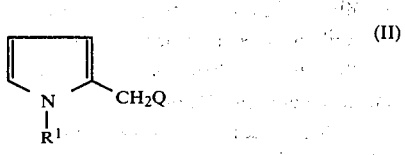

wherein $R^1$ is as defined above in this method, and Q is a facile leaving group, with imidazole.

Q is preferably $-N^{\oplus}$(lower alkyl)$_3$.

In a typical procedure, the compound of the formula (II) and imidazole are heated together, e.g. under reflux, in a suitable solvent, e.g. ethanol, for up to about 7 hours. The product may be isolated and purified by conventional procedures.

The starting materials of the formula (II) are either known compounds or may be prepared by conventional procedures, e.g.:

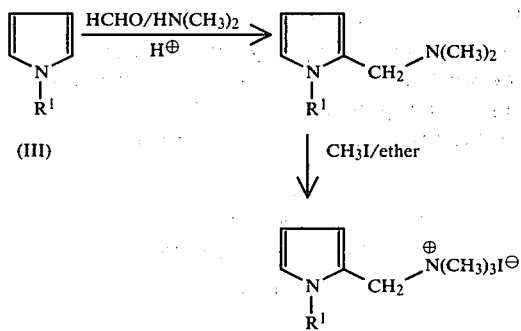

The pyrroles (III) are again either known compounds or may be prepared by conventional procedures, e.g.:

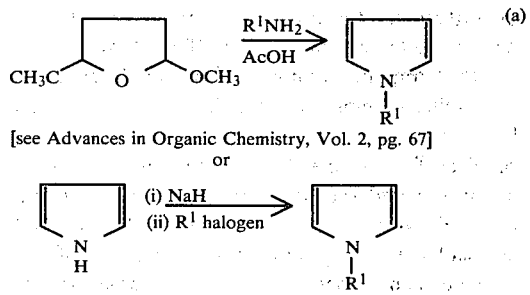

[see Advances in Organic Chemistry, Vol. 2, pg. 67]

or

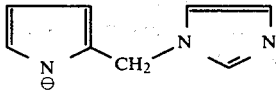

(2) The compounds of the invention in which $R^1$ is other than phenyl may be prepared by treating the compound of the formula (I) in which $R^1$ is hydrogen with a base such as sodium hydride which forms the anion:

and then reacting with an appropriate alkylating or acylating agent.

In a typical procedure, a dispersion of sodium hydride in oil is added cautiously to a solution of the pyrrole in a suitable solvent, e.g. N,N-dimethylformamide. After stirring, the appropriate alkylating or acylating agent in e.g. N,N-dimethylformamide is carefully added, and the resulting solution stirred at room temperature for up to about 20 hours. The product may be isolated and purified by conventional procedures.

Typical alkylating and acylating agents are alkyl and alkanoyl chlorides or bromides of the formula $R^1Cl$ or $R^1Br$.

(3) The compounds of the formula (I) in which X or Z are carboxy can be prepared by the alkaline hydrolysis of the corresponding lower alkoxycarbonyl compound.

(4) The compound of the formula (I) in which $R^1$ is 2-cyanoethyl can be prepared by the Michael addition from 2-(imidazol-1-ylmethyl) pyrrole and acrylonitrile in the presence of a base, e.g. benzyltrimethylammonium hydroxide.

The 2-cyanoethyl compound can then be hydrolysed in aqueous alkaline solution to the corresponding 2-carboxyethyl compound.

(5) The pharmaceutically acceptable acid addition salts may be prepared by conventional procedures, e.g. by reacting the free base in a suitable solvent with a solution of the appropriate acid in a suitable solvent, thus generally precipitating the desired salt.

The compounds of the invention inhibit the action of the thromboxane synthetase enzyme, but do not significantly inhibit the action of the prostacyclin synthetase or cyclo-oxygenase enzymes. Thus the compounds are useful in the treatment of conditions characterised by an imbalance of prostacyclin/thromboxane $A_2$, which may for example include thrombosis, ischaemic heart disease, stroke, transient ischaemic attack, migraine, and the vascular complications of diabetes, as explained below.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994; Nature, 1976, 263, 663; Prostaglandins, 1976, 12, 897). In most cases the prostaglandins $PGE_2$, $PGF_2$ and $PGD_2$ are comparatively minor by-products in this bio-synthetic pathway. The discovery of thromboxane $A_2$ and prostacyclin has significantly increased our understanding of vascular homeostasis; prostacyclin for instance is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685; Science, 1976, 17; Nature, 1978, 273, 765).

Thromboxane $A_2$ is synthetised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18; Prostaglandins, 1978, 13, 3). Alteration of the prostacyclin/thromboxane balance in favour of the latter substance could result in platelet aggregation, vasospasm (Lancet, 1977, 479; Science 1976, 1135; Amer. J. Cardiology, 1978, 41, 787) and an increased susceptibility to atherothrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. Aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extra-cerebral blood flow, in particular a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only is an abnormality of platelet function a major factor in the pathogenesis of migraine attacks but it is in fact their prime cause (Lancet (i), 1978 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism, 1979, 28, 394, Lancet 1978, (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds U. K. April, 1979). Also it has been shown that in rats with experimental diabetes vascular prostacyclin production is impaired and $TxA_2$ synthesis from the platelets is elevated (IV International Prostaglandin Conference, Washington, D.C. May 1979).

Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England J. Med., 1978, 299, 53; B.M.J., 1978, 1188; stroke, 1977, 8,301).

Although some encouraging results have been obtained with these drugs, a compound which specifically inhibits thromboxane $A_2$ formation leaving the biosynthesis of prostacyclin unimpaired would be more valuable in these clinical conditions (Lancet (ii), 1978, 780).

The effect of the compounds of the formula (I) on the thromboxane synthetase enzyme, and the prostacyclin synthetase and cyclo-oxygenase enzyme has been measured by the following in vitro enzyme assays:

1. Cyclo-oxygenase

Ram seminal vesicle microsomes (Biochemistry, 1971, 10, 2372) are incubated with arachidonic acid ($10^r$ $\mu M$: 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45, 451)) which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound, and following pre-incubation of the enzyme with the test compound for 5 minutes.

2. Prostacyclin ($PGI_2$) Synthetase

Pig aorta microsomes (Nature, 1976, 263, 663) are incubated (30 sec.; 22° C.) with $PGH_2$ produced as in 1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroperoxy-arachidonic acid (Prostaglandins, 1976, 12, 715). The test compound is then pre-incubated with the enzyme for 5 minutes, and its ability to prevent the decrease in tension is measured.

3. Thromboxane $A_2$ ($TxA_2$) Synthetase

Indomethacin pretreated human platelet microsomes (Science 1976, 193, 163) are incubated (2 min.: 0° C.) with $PGH_2$ (produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with the enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme.

The results of these tests are shown in the following Table, which gives the molar concentration of each compound which caused a 50% change in the effect of the relevant enzyme on isometric tension, i.e. caused a 50% inhibition of the action of that enzyme.

| R¹ | Molar concentration causing 50% inhibition of: | | |
|---|---|---|---|
| | TxA₂ Synthetase | PGI₂ Synthetase | Cyclo-oxygenase |
| —CH₂CH=CH₂ | $1.5 \times 10^{-7}$ | | |
| —CH₂CH₂CO₂H | $1.8 \times 10^{-7}$ | | |
|  | $6.2 \times 10^{-7}$ | | |
|  | $1.9 \times 10^{-9}$ | $6.5 \times 10^{-6}$ | |
| —CH₂— | $1.7 \times 10^{-6}$ | | |
| —CH₂——CO₂C₂H₅ | $2.4 \times 10^{-9}$ | $2.2 \times 10^{-5}$ | |
| —CH₂——CO₂H | $3.4 \times 10^{-9}$ | $10^{-4}$ | $>10^{-4}$ |
| —CO— | $4.9 \times 10^{-9}$ | $3.5 \times 10^{-5}$ | |

The results given in the Table show that all of the compounds tested caused a 50% inhibition of the thromboxane synthetase enzyme at a molar concentration of $1.7 \times 10^{-6}$ or less. Of the compounds tested for inhibition of the prostacyclin synthetase enzyme, none caused 50% inhibition at a molar concentration less than about 2,500 times greater than that at which they caused 50% inhibition of the thromboxane synthetase enzyme, i.e. they were all at least 2,500 times more potent as inhibitors of thromboxane synthetase than of prostacyclin synthetase. Of the compound tested for inhibition of the cyclooxygenase enzyme, its ability to inhibit this enzyme was at least 30,000 times less than its ability to inhibit the thromboxane synthetase enzyme.

In addition to the above an in vitro assay for measuring the inhibition of human blood platelet aggregation has been described and this may be predictive of anti-thrombotic efficacy clinically (Lancet (ii), 1974, 1223: J. Exp. Med., 1967, 126 (171). Both the clinically effective agents aspirin and sulphinpyrazone show inhibitory activity in vitro against a variety of aggregating agents in this test.

A number of in vivo tests in animals have also been described for evaluating potential anti-thrombotic drugs. Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138). The compounds of the invention are expected to be effective inhibitors of human blood platelet aggregation in the above in vitro assay, to protect rabbits against the lethal effect of arachidonic acid injection, and to prevent aggregation of platelets in the rat aorta.

The compounds may be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to tablets of the desired size. The capsules are typically prepared by granulating the ingredients together and filling them into hard gelatine capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes such as tonic and pH adjusters. The compounds may e.g. be added to distilled water and the pH adjusted to 3–6 using an acid such as citric, lactic or hydrochloric. Sufficient solutes such as dextrose or saline may be added to render the solution isotonic.

The resulting solution may then be sterilized according to the method of British Pharmacopoeia 1973 by filtration through a bacteria-proof filter under aseptic conditions into sterile containers so as to comply with the test for sterility of Appendix 121, British Pharmacopoeia 1973. Suitable containers are for example sterile glass vials of an appropriate size to contain the desired volume of solution, which volume will typically contain a unit dose of the compound of the formula (I). The compounds of the invention may also be administered by the infusion of a parenteral formulation as described above into a vein.

For oral administration to human patients, it is expected that the daily dosage level of a compound of the invention will be from 0.1 to 20 mg/kg per day for a typical adult patient (70 kg). For parenteral administration, it is expected that the daily dosage level of a compound of the formula (I) will be from 0.01–0.5 mg/kg. per day, for a typical adult patient. Thus tablets or capsules can generally be expected to contain from 5 to 150 mg of the active compound for administration orally up to 3 times a day. Dosage units for parenteral administration can be expected to contain from 0.5–35 mg of the active compound. A typical vial could be a 10 ml vial containing 5 mg of the active compound in 6–10 ml of solution.

It should of course be appreciated that the physician in any event will determine the actual dosage which will be most suitable for the individual and it will vary with the age, weight and response of the patient. The above dosages are exemplary of the average host. There may of course be individual cases where higher or lower dosage ranges are merited.

The following Examples, in which all temperatures are given in °C., illustrate the invention:

EXAMPLE 1

A. 2-(Imidazol-1-ylmethyl)pyrrole

A solution of 2-(dimethylaminomethyl)pyrrole (24.8 g) and imidazole (13.6 g) in xylene (120 ml) are heated under reflux for 3 hours. The solution was cooled and the solid was filtered off and crystallised from ether to give 2-(imidazol-1-ylmethyl) pyrrole (15.3 g), m.p. 89°–90°, raised to 91°–92° on further crystallisation from water.

Analysis %: Found: C, 65.65; H, 6.16; N, 28.95.
C₈H₉N₃ requires: C, 65.28; H, 6.16; N, 28.55.

B. 1-Benzyl-2-(imidazol-1-ylmethyl)pyrrole hydrochloride

Sodium hydride (1.44 g of 50% dispersion in oil) was added cautiously to a stirred solution of 2-(imidazol-1-ylmethyl)pyrrole (4.0 g) in dry N,N-dimethylformamide (70 ml) at 0°. The mixture was stirred at 0° for 30 minutes and then a solution of benzyl bromide (4.65 g) in dry N,N-dimethylformamide (30 ml) was added dropwise so that the temperature did not exceed 10°. The mixture was stirred at room temperature for 3 hours and then evaporated to small bulk. The residue was poured into water and the mixture was extracted with ethyl acetate (3×50 ml).

The combined extracts were washed with water and dried (MgSO₄). Evaporation of the solvent gave an oil which was chromatographed on silica gel. The column was first eluted with petrol (b.p. 40°-60°) to remove mineral oil an then with chloroform to give the product as an oil. The oil was dissolved in a small volume of ethanol and an excess of ethereal hydrogen chloride was added. The solid was filtered off and crystallised twice from ethanol/petrol (b.p. 60°-80°) to give 1-benzyl-2-(imidazol-1-ylmethyl)pyrrole hydrochloride (2.15 g), m.p. 154°-156°.

Analysis %: Found: C, 65.46; H, 5.78; N, 15.40.
C₁₅H₁₅N₃.HCl requires: C, 65.81; H, 5.89; N, 15.35.

EXAMPLES 2–10

The following compounds were prepared similarly to Example 1B, starting from 2-(imidazol-1-ylmethyl)pyrrole and sodium hydride in dimethylformamide and the appropriate alkylating or acylating agent.

| Example No. | R¹ | Q¹ | m.p. °C. | Recrystallisation Solvent | Found Analysis % C | H | N | Formula | Required Analysis % C | H | N |
|---|---|---|---|---|---|---|---|---|---|---|---|
| 2 | CH₂CH=CH₂ | Br | 115–118 | Isopropanol/ | 58.65 | 6.29 | 18.73 | C₁₁H₁₃N₃ · HCl | 59.05 | 6.30 | 18.78 |
| 3 | CH₂–<cyclopropyl> | Br | 116–118 | Isopropanol/Ether | 59.11 | 7.00 | 17.66 | C₁₂H₁₅N₃ · HCl · ½H₂O | 59.49 | 6.87 | 17.35 |
| 4 | CO–<phenyl> | Cl | 131–132 | Ethanol/Petrol (b.p. 60–80°) | 66.71 | 5.01 | 13.92 | C₁₅H₁₃N₃O · ½C₄H₄O₄* | 66.22 | 4.88 | 13.58 |
| 5 | CO–<phenyl>–CH₃ | Cl | 162–164 | Ethanol/Petrol (b.p. 60–80°) | 62.99 | 5.01 | 11.07 | C₁₆H₁₅N₃O C₄H₄O₄⁺ | 62.98 | 5.02 | 11.02 |
| 6 | CO–<phenyl>–OCH₃ | Cl | 87–89 | Ethyl Acetate/Petrol (b.p. 60–80°) | 67.90 | 5.47 | 14.88 | C₁₆H₁₅N₃O₂ | 68.31 | 5.37 | 14.94 |
| 7 | CO–<phenyl-OCH₃> | Cl | 91–93 | Ethyl Acetate | 67.76 | 5.35 | 14.72 | C₁₆H₁₅N₃O₂ | 68.31 | 5.37 | 14.94 |
| 8 | CO–<phenyl>–Cl | Cl | 123–125 | Ethyl Acetate/Petrol (b.p. 60–80°) | 63.12 | 4.27 | 14.36 | C₁₅H₁₂ClN₃O | 63.05 | 4.23 | 14.71 |
| 9 | –COCH₃ | Cl | | | | | | | | | |
| 10 | –CO–<cyclopropyl> | Cl | | | | | | | | | |

*hemifumarate
⁺fumarate

EXAMPLE 11

1-Phenyl-2-(imidazol-1-ylmethyl)pyrrole hydrochloride

A solution of [1-phenyl-pyrrol-2-yl]methyl trimethylammonium iodide (J.A.C.S., 73, 4921, (1951) (3.42 g) and imidazole (0.68 g) in ethanol (70 ml) was heated under reflux for 7 hours. The solution was evaporated and the residue was chromatographed on silica gel. Elution with chloroform gave an oil which was dissolved in ether. Addition of an excess of ethereal hydrogen chloride gave a precipitate which was filtered off and crystallised from methanol/ethyl acetate to give 1-phenyl-2-(imidazol-1-ylmethyl) pyrrole hydrochloride (0.65 g), m.p. 140°-141°.

Analysis %: Found: C, 64.34; H, 5.44; N, 15.94.
C₁₄H₁₃N₃.HCl requires: C, 64.74; H, 5.43; N, 16.18.

EXAMPLE 12

A. 1-Cyclohexyl-2-dimethylaminomethylpyrrole

A solution of dimethylamine hydrochloride (3.76 g) in 40% aqueous formaldehyde (3.5 ml) was added over 30 minutes to a stirred solution of 1-cyclohexylpyrrole in ethanol (25 ml) and the resulting solution was stirred at room temperature for 18 hours. Evaporation of the solution gave a solid which was dissolved in water. The solution was extracted with ether and then basified to pH 9-10 with 1 N sodium hydroxide solution. The resulting oil was extracted with ether (3×50 ml) and the combined ethereal extracts were washed with water and dried (MgSO$_4$). Evaporation of the ether gave an oil which was chromatographed on silica gel. Elution with chloroform gave 1-cyclohexyl-2-(dimethylaminomethyl)pyrrole (5.0 g) as an oil.

Analysis %: Found: C, 75.28; H, 10.98; N, 13.19. $C_{13}H_{22}N_2$ requires: C, 75.67; H, 10.75; N, 13.58.

B. [1-Cyclohexyl-pyrrol-2-yl]methyl trimethylammonium iodide

A solution of methyl iodide (3.55 g) in dry ether (20 ml) was added dropwise to a stirred solution of 1-cyclohexyl-2-dimethylaminomethylpyrrole (4.12 g) in dry ether (50 ml) at 5°. The resulting mixture was stirred at room temperature for 5 hours and then allowed to stand overnight. The solid was filtered off, washed with ether and dried to give [1-cyclohexyl-pyrrol-2-yl]methyl trimethylammonium iodide (6.0 g), m.p. >250° (darkening ca. 190°).

Analysis %: Found: C, 48.25; H, 7.18; N, 7.78. $C_{14}H_{25}IN_2$ requires: C, 48.28; H, 7.24; N, 8.05.

C. 1-Cyclohexyl-2-(imidazol-1-ylmethyl)pyrole imidazole hydrochloride

A solution of (1-cyclohexyl-pyrrol-2-yl)methyl trimethylammonium iodide (3.48 g) and imidazole (0.68 g) in ethanol (70 ml) was heated under reflux for 3 hours. The solution was evaporated and the residue was chromatographed on silica gel. Elution with chloroform gave an oil which was dissolved in ether. An excess of ethereal hydrogen chloride was added and the resulting solid was filtered off and crystallised from methanol/ethyl acetate to give 1-cyclohexyl-2-(imidazol-1-ylmethyl) pyrrole hydrochloride as a hygroscopic solid (0.80 g), m.p. 147°-149°.

Analysis %: Found: C, 60.67; H, 7.35; N, 15.14. $C_{14}H_{19}N_3.HCl.\frac{1}{2}H_2O$ requires: C, 61.18; H, 7.70; N, 15.29.

EXAMPLE 13

A. 1-(2-Cyanoethyl)-2-(imidazol-1-ylmethyl)pyrrole 2-(Imidazol-1-ylmethyl)pyrrole (4.41 g) and acrylonitrile (6.0 ml) were dissolved in dioxan (75 ml) and benzyltrimethylammonium hydroxide (1.5 ml of 40% solution in methanol) was added. The mixture was warmed to 55° for 1 hour and then allowed to stand at room temperature for 18 hours. It was then poured into water and the mixture was extracted with ethyl acetate. The combined ethyl acetate extracts were washed with water and dried (Na$_2$SO$_4$). Evaporation of the solvent gave an oil which was chromatographed on silica gel. Elution with chloroform gave 1-(2-cyanoethyl)-2-(imidazol-1-ylmethyl)pyrrole (5.0 g) as an oil.

B. 1-(2-Carboxyethyl)-2-(imidazol-1-ylmethyl)pyrrole

The above oil (2.5 g) was heated on a steam bath for 4 hours in 10% aqueous potassium hydroxide (25 ml). The solution was cooled and just acidified with acetic acid and then evaporated and the residue was chromatographed on silica gel. Elution with a mixture of chloroform and methanol (15:1) gave an oil which solidified on scratching. The solid was crystallised from methanol/ethyl acetate to give 1-(2-carboxyethyl)-2-(imidazol-1-ylmethyl)pyrrole (0.55 g), m.p. 127°-128°.

Analysis %: Found: C, 60.00; H, 6.05; N, 19.08. $C_{11}H_{13}N_3O_2$ requires: C, 60.26; H, 5.98; N, 19.15.

EXAMPLE 14

1-(4-Carbethoxybenzyl)-2-(imidazol-1-ylmethyl)pyrrole maleate 2-(Imidazol-1-ylmethyl)pyrrole (4.0 g) was dissolved in dry N,N-dimethylformamide (50 ml) and cooled to 0°. Sodium hydride (1.44 g of 50% dispersion in mineral oil) was added and the mixture was stirred at 0° for 30 minutes. A solution of ethyl 4-bromomethylbenzoate (6.61 g) in dry N,N-dimethylformamide (20 ml) was added with stirring over 10 minutes and the resulting mixture was stirred at room temperature for 20 hours. Water (2 ml) was added to decompose excess sodium hydride and the mixture was evaporated. The residue was chromatographed on silica gel. The column was eluted first with petrol (b.p. 40°-60°) to remove mineral oil and then with chloroform to give the product (7.0 g) as an oil.

A portion was dissolved in ether and an excess of an ethereal solution of maleic acid was added. The solid was filtered off and crystallised from ethyl acetate/ether to give 1-(4-carbethoxybenzyl)-2-(imidazol-1-ylmethyl)pyrrole maleate, m.p. 98°-99°.

Analysis %: Found: C, 61.90; H, 5.56; N, 10.23. $C_{18}H_{19}N_3O_2.C_4H_4O_4$ requires: C, 62.16; H, 5.45; N, 9.88.

EXAMPLE 15

1-(4-Carboxybenzyl)-2-(imidazol-1-ylmethyl)pyrrole

A solution of sodium hydroxide (0.20 g) in water (20 ml) was added to a solution of 1-(4-carbethoxybenzyl)-2-(imidazol-1-ylmethyl) pyrrole (1.55 g) in ethanol (20 ml) and the mixture was heated under reflux for 8 hours. The solution was evaporated and the residue was taken up in water (25 ml). The solution was acidified with acetic acid and continuously extracted with chloroform to give a solid which was crystallised from isopropanol to give 1-(4-carboxybenzyl)-2-(imidazol-1-ylmethyl)pyrrole (0.50 g), m.p. 190°-191° (d).

Analysis %: Found: C, 68.51; H, 5.47; N, 14.89. $C_{16}H_{15}N_3O_2$ requires: C, 68.31; H, 5.38; N, 14.94.

We claim:

1. A compound of the formula

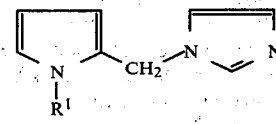

wherein R$^1$ is lower cycloalkyl, lower cycloalkyl-lower alkyl, lower alkenyl-lower alkyl, lower alkanoyl, phenyl, lower cycloalkylcarbonyl, or a group of the formula

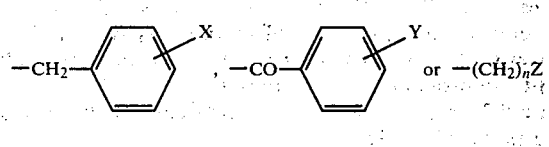

wherein

X is hydrogen, carboxy or lower alkoxycarbonyl;

Y is hydrogen, lower alkyl, lower alkoxy or halogen, n is an integer of from 1 to 4; and Z is cyano, carboxy or lower alkoxycarbonyl; and the pharmaceutically acceptable acid addition salts thereof.

2. A compound of claim 1 wherein $R^1$ is lower cycloalkyl, lower cycloalkyl-lower alkyl, lower alkenyl-lower alkyl, lower alkanoyl, phenyl, benzyl or a group of the formula

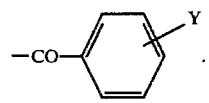

3. A compound of claim 1 wherein $R^1$ is allyl; cyclopropylmethyl; benzoyl; benzoyl monosubstituted by methyl, methoxy or chloro; acetyl; cyclopropylcarbonyl; phenyl; cyclohexyl; 2-cyanoethyl; 2-carboxyethyl; benzyl; or benzyl monosubstituted on the phenyl ring by carboxy or ethoxycarbonyl.

4. A compound of claim 1 wherein $R^1$ is

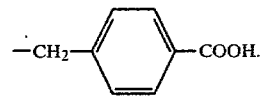

5. A pharmaceutical composition useful in selectively inhibiting the action of thromboxane synthetase enzyme comprising a pharmaceutically acceptable carrier and a compound of claim 1 in an amount effective to inhibit the action of thromboxane synthetase enzyme in an animal.

6. A pharmaceutical composition of claim 5 wherein $R^1$ is

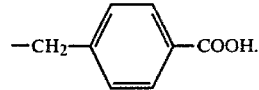

7. A method of selectively inhibiting the action of thromboxane synthetase enzyme in an animal comprising administering to said animal an effective amount of a compound of claim 1.

8. A method of claim 7 wherein $R^1$ is

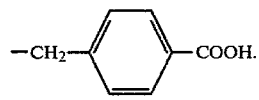

* * * * *